United States Patent [19]
Hillion et al.

[11] Patent Number: 5,756,471
[45] Date of Patent: May 26, 1998

[54] USE OF A SOPHOROLIPID TO PROVIDE FREE RADICAL FORMATION INHIBITING ACTIVITY OR ELASTASE INHIBITING ACTIVITY

[75] Inventors: Gérard Hillion, Herblay; Rémy Marchal, Chatou; Corinne Stoltz, Dammarie Les Lys; Frédérique Borzeix, Rueil Malmaison, all of France

[73] Assignees: Institut Francais du Petrole; Sophor S.A., both of Rueil-Malmaison, France

[21] Appl. No.: 750,618
[22] PCT Filed: Jun. 12, 1995
[86] PCT No.: PCT/FR95/00768
§ 371 Date: Dec. 13, 1996
§ 102(e) Date: Dec. 13, 1996
[87] PCT Pub. No.: WO95/34282
PCT Pub. Date: Dec. 21, 1995

[30] Foreign Application Priority Data

Jun. 13, 1994 [FR] France ................. 94 07287

[51] Int. Cl.$^6$ ................. A61K 31/70
[52] U.S. Cl. ................. 514/25; 514/53
[58] Field of Search ................. 514/25, 53

[56] References Cited

U.S. PATENT DOCUMENTS 4,216,311  8/1980  Inoue et al. ................. 536/115

FOREIGN PATENT DOCUMENTS 0209783  1/1987  European Pat. Off. .

OTHER PUBLICATIONS

"Dorland's Pocket Medical Dictionary" W.B. Saunders Company, Philadelphia, PA. 1989, pp. 160 and 168.
Abstract, Week 8008, AN 80–13763C, Database WPI, Derwent Publications Ltd., (JP–A–55 004 344), Feb. 1980.

Primary Examiner—Kathleen K. Fonda
Attorney, Agent, or Firm—Millen, White, Zelano, & Branigan, P.C.

[57] ABSTRACT

The present invention relates to a cosmetic and/or dermatological composition comprising at least one sophorolipid in its crude or acid form or associated with a monovalent or divalent salt. The concentrations of the sophorolipid can be 0.01% to 30% by weight. In particular, the composition is in the form of a water-in-oil emulsion, and oil-in-water emulsion or an oil-in-water microemulsion. The sophorolipid-based compositions of the invention have a free radical formation inhibiting activity, an elastase inhibiting activity, or an anti-inflammatory activity.

18 Claims, No Drawings

USE OF A SOPHOROLIPID TO PROVIDE FREE RADICAL FORMATION INHIBITING ACTIVITY OR ELASTASE INHIBITING ACTIVITY

This application is the U.S. national stage entry under 35 U.S.C. 371 of PCT/FR95/00768, filed Jun. 12, 1995.

The present invention concerns a novel use of sophorolipids.

The present invention also concerns cosmetic or dermatological compositions.

More particularly, the present invention concerns such compositions with anti-radical and anti-elastasic properties. Such properties are of particular use in compositions intended for skin care and for hair care.

Sophorolipids are glycolipids; they are produced by fermentation of Candida or Torulopsis type yeasts such as *Torulopsis magnoliae, Candida bombicola, Candida apicola* or *Candida bogoriensis*.

The constituent glucide of extracellular sophorolipids is sophorose (2'-O-βD-glucopyranosyl-β-D-glucopyranose). This sugar can be acetylated in the 6' and 6" position and is bonded to a fatty hydroxy-acid in the ω or ω-1 position.

The lipid fraction of sophorolipids, composed of several fatty hydroxy-acids, which differ from each other by their chain length, by the number and position of the unsaturations, and by the hydroxylation position, depends on the lipid composition of the secondary carbon source used in fermentation (vegetable oil of variable richness in saturated or unsaturated lipids).

Such glycolipids are synthesised in the form of a mixture of several classes of sophorolipids which differ by their degree of saturation or unsaturation, by the presence or absence of several types of lactonisation and by their different degrees of acetylation.

The different classes of sophorolipids are as follows:

1. Lactones, acetylated or not in the 6' and 6" position of the sophorose:
   sophorolipid 1',4"-lactone 6'-6" diacetate (notation: Sl-4" L6'a6"a);
   sophorolipid 1',4"-lactone 6" mono-acetate (notation: Sl-4" L6"a);
   sophorolipid 1',4"-lactone (notation: Sl-4" L);

2. Acids, acetylated or not in the 6' position of the sophorose:
   acid sophorolipid -6'- monoacetate (notation: Sl-A6' a);
   acid sophorolipid (notation: Sl-A).

Two chemical formulae which represent the lactone and acid forms of sophorolipids are shown below:

Lactone forms (I)

[Chemical structure]

-continued
and Acid forms (II):

[Chemical structure]

where R=H or $CH_3$—CO.

These chemical formulae illustrate the case of the most abundant fatty hydroxy-acid, 17-hydroxyoctadecenoic acid (17-hydroxyoleic acid).

The respective contributions of each constituent hydroxy-acid, as determined using gas chromatography for the different classes of sophorolipids, also the distributions of these classes, are shown below.

The constituent fatty hydroxy-acids of sophorolipids are, for example, as follows:

| Types | Fatty hydroxy-acids | % |
|---|---|---|
| C 16:0 | 15-OH Hexadecanoic | 1.5 |
| C 16:0 | 16-OH Hexadecanoic | 2.0 |
| C 18:0 | 17-OH Octadecanoic | 3.5 |
| C 18:1 | 17-OH Octadecenoic | 60.0 |
| C 18:1 | 18-OH Octadecadienoic | 12.0 |
| C 18:2 | 17-OH Octadecadienoic | 7.0 |
| C 18:2 | 18-OH Octadecadienoic | 14.0 |

The principal biosynthetic glycolipid production route is carried out using triglycerides or carbohydrates.

The production of glycolipids using micro-organisms does not require the supplemental addition of nitrogen and salt; it takes place when the cell finds a sufficient source of carbon and oxygen.

Glycolipid biosynthesis includes the synthesis of the lipophile portion (fatty acid) and the hydrophilic portion (sophorose).

Glycolipid biosynthesis is characterized by the following factors:

synthesis of the lipid portion depends on the hydrophobic carbon source (oil) used as the substrate;

synthesis of the glucidic portion also depends on the carbon source used, but is synthesised de novo.

Yeasts from the genus Torulopsis, such as *T. magnoliae* or *T. bombicola* (currently classed in the genus Candida) excrete sophorolipids if they are cultivated in the presence of 10% of glucose, 1.25% of yeast extract and 0.2% of urea, for example.

Studies have shown that the rate of sophorolipid production can be increased by addition of esterified long chain fatty acids or n-alkanes or triglycerides to the culture medium.

Processes for the production of acetylated sophorolipids in their acid form by culture of a strain of *Candida bombicola* or *Candida apicola* use a substrate consisting of a vegetable oil.

Surfactants are used for body care, dental care, in washing agents and in the pharmaceutical industry as well as in the cosmetics industry. In view of their increasing use, current ecological considerations have led to the study of the biological and toxic properties of these substances. Thus it is known that synthetic surfactants (i.e., non biological surfactants) modify the permeability of biological membranes. Cationic and anionic surfactants have an effect on intracellular molecule liberation or inhibit respiration. Depending on their concentration, synthetic surfactants can also have a toxic effect.

One aim of the present invention is to provide non toxic biological surfactants in cosmetic or pharmaceutical compositions.

Sophorolipids have been used as a biodegradable industrial detergent, in particular in depollution processes such as those described in French patent applications 92/16033 and 93/14999 and European patent application EP-A-0 499 434.

Patent application EP-A-0 209 783 (Wella) describes the lactone form of sophorolipids and its use as an antidandruff and bacteriostatic agent.

Japanese patent application JP-A-55 004344 (Kao) mentions an ester of a glycolipid hydroxyalkyl ether used in cosmetics.

None of these applications either describes or suggests a composition with an anti-radical, anti-elastasic and/or anti-inflammatory property.

Further, cosmetic and pharmaceutical compositions based on glycolipids such as glycosylceramides or digalactodiglycerides have been proposed for bringing the benefit of lipids to the skin, in particular with a view to skin moisturisation.

In the present invention, we have discovered that sophorolipids are glycolipids which have advantageous physico-chemical properties, in particular multiple emulsifying properties which can allow the preparation of highly diverse formulations based on sophorolipids which can be used in cosmetics or for topical applications in general.

Further, we have discovered that these sophorolipids, in addition to providing the skin with all the benefits of lipids, have anti-radical and anti-elastasic properties which are precisely those which are desirable in compositions for cosmetic, hygienic or pharmaco-dermatological use, in particular for the protection and care of the hair or skin.

Thus the aim of the present invention is the use of sophorolipids for the preparation of a cosmetic or dermatological composition, and the composition obtained.

The present invention thus proposes, for the first time, surfactant glycolipids of biological origin with multiple emulsifying properties and with anti-radical, anti-elastasic and/or anti-inflammatory properties.

In accordance with the present invention, sophorolipids which, because of their particular emulsifying properties, allow the preparation of cosmetic compositions in the form of continuous aqueous phase emulsions (oil-in-water emulsion) or continuous oil phase emulsions (water-in-oil emulsion) provide the skin or hair with lipids without necessarily requiring the use of synthetic surfactants and emulsifying agents. These compositions are of particular use as vectors for the active ingredient of medication.

In accordance with the present invention, the sophorolipids can also produce stable continuous oil phase emulsions in which the oleophilic phase can be of entirely plant origin when the substrate used for sophorolipid production by fermentation is a vegetable oil and when the oleophilic phase comprises a vegetable oil such as olive oil, sweet almond oil, walnut oil or hydrogenated coconut oil, etc. The use of products of plant origin rather than of animal origin is particularly desirable in order to avoid toxicological problems.

Finally, when they are used in the acid form or in the monovalent metallic salt form, such as a sodium or potassium salt, or a divalent salt of the acid, sophorolipids constitute an anionic surfactant with HLB values which vary depending on the pH, by means of which, for high HLB values, in particular at about 8 to 12, it is possible to obtain stable aqueous emulsions and even stable aqueous microemulsions and high clarity (HLB of about 13 to 15), which is a desirable property for the preparation of certain cosmetic and sanitary compositions.

In particular, aqueous microemulsions (oil-in-water microemulsions) are important for the production of fragrancing lotions or eaux de toilette without using a hydroalcoholic solution, i.e., without using alcohol.

In one advantageous embodiment of the present invention, the compositions comprise a sophorolipid as the sole emulsifying agent. However, a synergistic effect can also be obtained by using a mixture of a conventional surfactant such as sodium dioctyl sulphosuccinate (DOS), ethoxylated nonylphenol, ethoxylated sorbitan monolaurate (Tween 20) or cetyl trimethyl ammonium, and sophorolipids, by reduction of the surface tension between the water and the hydrocarbons.

In the compositions of the invention, however, the sophorolipids are preferably purified to obtain the sophorolipids in only their acid and/or salt form, which is more stable than the lactone forms. Stability is important from an olfactory viewpoint. The lactone forms are particularly non-soluble in aqueous solution while the acid forms and/or their salts are soluble in aqueous solution.

The sophorolipids used in the present invention are preferably obtained by fermenting $C.$ $bogoriensis$ or $C.$ $bombicola$. Particular examples are sophorolipids with formulae [1] (acid form) and [2] (lactone form) shown below, where $R^1$ is hydrogen or an acetyl group and $R^2$ is hydrogen or an alkyl group containing 1 to 9 carbon atoms when $R^2$ is a saturated hydrocarbon residue containing 7 to 16 carbon atoms, or $R^2$ is hydrogen or a methyl group when $R^3$ is an unsaturated hydrocarbon residue containing 13 to 17 carbon atoms;

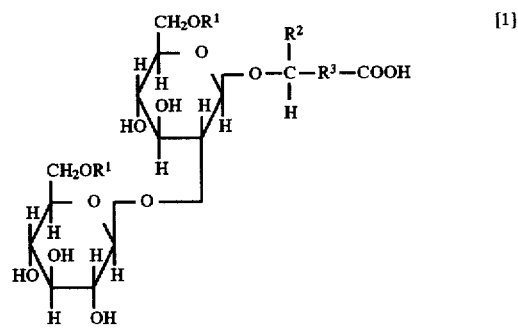

and

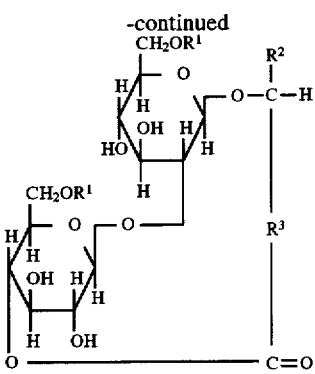

[2]

in particular, —R²CH—R³— is a divalent residue of a saturated or unsaturated $C_{16}$ or $C_{18}$ fatty hydroxyacid with one or two double bond(s) as mentioned above.

The compositions of the invention contain 0.01% to 30% (w/w) of sophorolipids (dry matter) of the total composition, more particularly 0.05% to 5% of sophorolipids (dry matter).

The compositions of the invention may comprise saturated or unsaturated $C_{10}$–$C_{34}$ fatty acids, preferably $C_{14}$–$C_{22}$, such as oleic, linoleic, linolenic, palmitic and palmitoleic acids, in an amount of 0.01% to 20% by weight with respect to the sophorolipids (dry matter), more particularly 1% to 10%, a major portion of which can be added subsequently depending on the envisaged use.

In particular embodiments, cosmetic compositions of the invention consist of:

- milks, in particular in the form of oleoalcoholic lotions, aqueous emulsions or aqueous microemulsions;
- lotions such as fragrancing lotions or eaux de toilette, in particular in the form of hydroalcoholic lotions, or stable aqueous microemulsions;
- shampoos, shower gels, or liquid soaps in the form of aqueous microemulsions;
- make-up removing gels, moisturizing creams, in particular in the form of water/oil or oil/water emulsions;
- solid grease mixtures such as a lipstick or an ointment.

These properties are of particular use for hair and skin care and hygiene.

The cosmetic compositions of the invention can be used for the anti-radical and/or anti-elastasic properties of the sophorolipids. In dermatology, they have anti-radical properties, anti-elastasic and/or anti-inflammatory properties.

In pharmaco-dermatological compositions, all composition formulations which can be topically applied can be used, in particular ointments, creams, milks, lotions, gels and liquid soaps.

Further advantages and characteristics of the present invention will become clear from the following examples.

Tables 10 and 11 show different possible formulations for compositions of the invention.

EXAMPLE 1

This illustrates synthesis conditions in strains of *Candida bombicola*.

The optimal sophorolipid production conditions were as follows: a culture medium was used which initially contained 10% of glucose, 0.5% of macerated dry corn liquor and 0.4% of ammonium sulphate. The pH of the culture medium was initially 6.0 and the incubation temperature was fixed between 22° C. and 30° C. A second carbon source was continuously added, for example alkanes, long carbon chain alcohols, fatty acids or their ethyl or methyl esters.

When fermentation was complete, the glucose/second carbon source consumption ratio was generally about 2:1.

With *C. bombicola* CBS 6009, 300 g/l of sophorolipids could be produced by continuously supplying the methyl (or ethyl) ester of rapeseed oil and daily addition of glucose as described in French patent FR-A-2 692 593.

The specifications of the crude and acid forms of the sophorolipids are given below:

1. Crude sophorolipids aspect: liquid, viscous
   odour: hardly any
   dry matter ≦60%±0.5%
   colour: amber
   free fatty acid: ≦4% (2.6% oleic acid)
   free sugar ≦1%
   mineral salts ≦2%
   pH: 7±0.5
   preservatives: phenoxyethanol, sodium-containing methyl parahydroxybenzoate

| | |
|---|---|
| density at 20° C. | 1.097 |
| density at 40° C. | 1.085 |
| kinematic viscosity: | 562.61 mm²/s: at 20° C. |
| | 160.49 mm²/s: at 40° C. |

The distribution of the constituent fatty hydroxyacids of the crude sophorolipids was as follows (Table 1).

| Fatty acids | % |
|---|---|
| 15-OH C16:0 | 1.7 |
| 16-OH C16:0 | 1.2 |
| 17-OH C18:2 | 6.7 |
| 17-OH C18:1 | 63.4 |
| 17-OH C18:0 | 3.2 |
| 17-OH C18:2 | 13.5 |
| 18-OH C18:1 | 10.3 |

2. Acid sophorolipids

Acid sophorolipids were obtained after alkaline hydrolysis of the crude sophorolipids.

aspect: liquid, slightly viscous
   odour: slightly acetylated
   water content: ≧60%±5%
   free fatty acid: ≦5% (2.4% oleic acid)
   free fatty hydroxyacid: ≦0.5%
   free sugar ≦1%
   minerals ≦2%
   preservatives: phenoxyethanol, sodium-containing methyl parahydroxybenzoate (MPOB, Na)
   pH: 6±0.5%

| | |
|---|---|
| density at 20° C. | 1.092 |
| density at 40° C. | 1.082 |
| kinematic viscosity: | 96 mm²/s: at 20° C. |
| | 42 mm²/s: at 40° C. |

The distribution of the constituent fatty hydroxyacids of the acid sophorolipids was as follows (Table 2).

| Hydroxyacids | Relative quantity (%) |
|---|---|
| 15-OH C16:0 | 0.5 |
| 16-OH C16:0 | 1.0 |
| 17-OH C18:0 | 4.0 |
| 17-OH C18:1 | 64.0 |
| 18-OH C18:1 | 10.0 |
| 17-OH C18:2 | 7.0 |
| 18-OH C18:2 | 13.5 |

EXAMPLE 2

1. Ocular tolerance

Crude 6% (dry matter) sophorolipid products and 4% (dry matter) acid sophorolipids were instilled in a single dose in an amount of 0.1 ml into the eye of three rabbits, using a protocol drawn from the official method defined in the Order of 9th Jun., 1992 (Journal Officiel de la Republique Francaise [Official Journal of the Republic of France], 10th Jul., 1992).

The scores produced a maximum irritation index of 15.0 and 7.3 one hour after installation for the crude and acid sophorolipid forms respectively.

The results of these tests lead to the conclusion that the crude sophorolipid and acid sophorolipid products are weak irritants.

2. Cutaneous tolerance.

Crude 6% (dry matter) sophorolipid products and 4% (dry matter) acid sophorolipids, diluted in distilled water, were applied in a dose of 0.5 ml to an area of healthy skin and to an area of scarified skin in three rabbits, using a protocol drawn from the official method defined in the Order of 1st Feb., 1982 (Journal Officiel de la Republique Francaise Official [Journal of the Republic of France], 21st Feb., 1982).

The scores recorded produced an index of 0.3 and 0.1 for the crude and acid sophorolipid forms respectively.

The results of these tests lead to the conclusion that crude sophorolipid products and acid sophorolipid products are not irritants.

3. Oral safety test

The aim of this study, carried out in accordance with the present protocol, was to evaluate the toxicity after a single oral administration of a maximal dose of sophorolipids.

The products, referred to as crude sophorolipids and acid sophorolipids, were administered to two batches of male and female rats in a dose of 5 ml/kg.

The methodology used for this study was derived from the protocol set out in OECD Directive 84/449 L251 of 25th Apr., 1984.

For each product which was separately tested, the mortality in the two batches of animals was zero.

Under these conditions, the crude sophorolipids and acid sophorolipids had an oral safety level which was greater than or equal to 5 ml/kg of weight.

4. Determination of sensitising power using Magnusson and Kligman

The aim of the study carried out using the present protocol was to evaluate the sensitising power of crude sophorolipids and acid sophorolipids on albino guinea pigs. Two weeks after a series of repeated contacts with the products of the study (induction phase), the guinea pigs received a triggering dose with the same products to establish whether a state of hypersensitivity had been induced.

Observations made following the triggering dose carried out with the products at maximal non irritating concentration allowed crude sophorolipids and acid sophorolipids to be placed in Class 1.

Under these conditions, crude sophorolipids and acid sophorolipids have a very low sensitising power which was not significant in albino guinea pigs.

5. Bacteriological examination and conservation study

One gram of sophorolipids was dissolved in 10 ml of sterilised water. 1 ml of this solution was then streaked onto Sabouraud gelose (SAB).

The streaks were placed in an oven at 37° C. for 120 hours; the colonies obtained were counted in CFU (colony forming units) and reduced to 1 g/ml of product.

The bacteriological conservation study of the product was carried out over 12 weeks (see Table 3 below).

The results obtained conformed to bacteriological standards.

| Storage conditions | Protective agents* | COUNT (CRU/ml) on SAB | | |
|---|---|---|---|---|
| | | t0 | t0 + 6 weeks | t0 + 12 weeks |
| 4° C. | – | 0 | $3.10^2$ | $4.10^2$ |
| 20° C. | – | 0 | 10 | 90 |
| 4° C. | + | 0 | 0 | 0 |
| 20° C. | + | 0 | 0 | 0 |

*0.5% phenoxyethanol
+0.5% MPOB, Na

EXAMPLE 3

Anti-elastasic Properties

Human leucocytic elastase (HLE) has been the subject of numerous studies as it intervenes in inflammatory pathologies such as pulmonary emphysema, rheumatoid polyarthritis and parodonthopathies. This enzyme can degrade a number of macromolecules in the conjunctive tissue: fibrous elastin, certain types of collagen, and structure proteoglycanes and glycoproteins. It thus appears to be vital to use anti-leucocytic elastase substances to prevent degradation of all of these macromolecules during inflammatory phenomena.

Human leucocytic elastase (HLE) inhibition test

The anti-elastasic properties of sophorolipids in aqueous solution were studied using HLE and N-methoxysuccinyl-alanine-alanine-proline-valine-P-nitroanilide as a synthetic substrate in a TRIS HCl buffer.

The kinetics were followed by spectrophotometry at 410 nm to study the liberation of P-nitroaniline (coloured product). The results are shown in Table 4 below:

| Inhibition of human leucocytic elastase by crude sophorolipids | |
|---|---|
| Sophorolipids (dry matter) mg/ml | % inhibition with respect to reference |
| 0.15 | 75 |
| 0.12 | 70 |
| 0.06 | 56 |
| 0.03 | 38 |
| 0.023 | 20 |
| 0 | 0 |

EXAMPLE 4

Anti-elastasic Properties (on human skin)

The anti-elastasic activity of crude sophorolipids was demonstrated on a human skin section.

The elastin substrate was that which exists in human skin. Elastase digests elastin (shown by histochemistry) and inhibition of the enzyme is demonstrated by a reduction in that digestion.

The reference molecule, mercury chloride, inhibits elastase activity in a dose-dependent manner. That result was expected and acted to validate the test.

Evaluation of the anti-elastase activity of crude sophorolipids on human skin is shown in Table 5.

| Compound | Concentration, % (w/v) | Degradation of elastin fibres |
|---|---|---|
| Buffer Control | 0 | None |
| mastase Control | 0 | Complete |
| Crude sophorolipids | 0.5 | Partial |
|  | 5 | None |
| $HgCl_2$ | 0.125 | None |

At 5% (w/v), crude sophorolipids completely inhibited the degradation of the elastin fibres.

EXAMPLE 5

Anti-elastasic Activity (test in semi-solid medium)

Principle: Inhibition of the degradation of elastin contained in gelose by elastase The anti-elastase activity of acid sophorolipids was evaluated using a semi-quantitative technique. The enzymatic solution, associated or otherwise with the test compound or with the reference molecule, was deposited in hollows in gelose containing the substrate, elastin.

The enzyme diffused into the gelose and digested the elastin.

This phenomenon was shown as a lightening of the gelose in the digestion zone, which zone was measured.

The effects of acid sophorolipids on elastin digestion by pancreatic elastase are shown in Table 6:

| Acid sophorolipids | percent digestion with respect to single enzyme reference (cm$^2$) Incubation | |
|---|---|---|
| (%) (w/v) | 6 hours | 21 hours |
| 0 | 100% | 100% |
| 0.4 | 74% | 67% |
| 2 | 63% | 53% |
| Concentration of reference inhibitor | Diameter of digestion zone (cm) Incubation | |
| ($HgCl_2$) | 6 hours | 21 hours |
| 10 mM | 0 | 0 |

The reference inhibitor which was tested in parallel was 10 mM mercury chloride. In the presence of that molecule, enzymatic inhibition was total (Table 7 above).

In the presence of the test product alone, the aspect of the gelose was not altered.

In the presence of acid sophorolipids, the digestion surface was reduced with respect to the reference for concentrations of 0.4% and 2%. After 6 hours of incubation, these surfaces were 0.28 cm$^2$ and 0.24 cm$^2$ respectively for the 0.4% and 2% concentrations. It was 0.38 cm$^2$ for the reference with no product. After 21 hours of incubation, these surfaces were 0.64 cm$^2$ and 0.5 cm$^2$ respectively for concentrations of 0.4% and 2%. It was 0.95 cm$^2$ for the reference enzyme with no product.

In conclusion, in this study, the acid sophorolipids at 0.4% concentration slightly inhibited elastin activity. This activity was much more strongly inhibited by the product at 2% concentration. This product can thus claim an anti-elastase activity at these concentrations.

EXAMPLE 6

Anti-radical activity (EPR method)

The anti-radical effect of crude and acid sophorolipids was evaluated with respect to a free radical derived from oxygen and which is particularly important in pathology, namely the hydroxyl radical.

Electron paramagnetic resonance spectrometry (EPR) was used.

In this method, the spin states of unpaired electrons in micro-organisms, in particular free radicals, are characterized.

A molecule which traps free radicals reduces the signal.

EPR measurements were carried out using a Brucker ECS106 spectrometer at ambient temperature.

The hydroxyl radical (OH·) was produced by photolysis (UVB) of hydrogen peroxide in aqueous solution.

Mannitol was used as a reference molecule (positive control).

In the presence of 10 mM of mannitol, the EPR signal is greatly reduced: the trapping activity rises to 98%.

Crude sophorolipids in concentrations of 0.0092% and 0.028% of dry matter (w/v) had a trapping effect of 71% and 97% respectively. Crude sophorolipids at 2.5% of dry matter (w/v) cancelled the EPR signal.

Acid sophorolipids from a concentration of 0.0092% of dry matter (w/v) showed a 98% trapping effect.

The effect of sophorolipids and mannitol on the intensity of the EPR signal corresponding to the hydroxyl radical is shown in Table 8.

| Compound | Concentration | % anti-radical protection |
|---|---|---|
| Reference | — | 0 |
| Crude sophorolipids | 2.5% | 100 |
|  | 0.083% | 100 |
|  | 0.028% | 97 |
|  | 0.0092% | 71 |
| Acid sophorolipid | 2.5% | 100 |
|  | 0.083% | 100 |
|  | 0.028% | 98 |
|  | 0.0092% | 98 |
| Mannitol | 0.182% | 98 |

The concentrations are expressed as the percentage by weight of dry matter/volume.

The reactive metabolites oxygen, superoxide anion ($O_2$), hydroxyl radical (OH·), hydrogen peroxide ($H_2O_2$) and singlet oxygen ($1O_2$) are responsible for toxic reactions in the organism. Whether produced by the organism itself or by external aggression, they degrade sugars, proteins, lipids and nucleic acids.

Acid and crude sophorolipids reduce the EPR signal of the hydroxyl radical in a dose-dependent manner. This effect is intense with respect to mannitol (the reference molecule known for its ability to trap OH·).

In conclusion, crude and acid sophorolipids exhibit considerable anti-radical effects towards the hydroxyl radical. These effects manifest themselves at the low concentrations which are generally used for formulations containing active cosmetic ingredients.

EXAMPLE 7

Anti-radical Effect (on human fibroblasts)

The protective effect of crude sophorolipids against free radicals generated by UVA was demonstrated on fibroblast cultures.

The tests were carried out on sophorolipid concentrations which were non toxic to the cells.

The reference molecule, the acetate of vitamin E, at a concentration of 200 µg/ml, was not toxic for cells in the absence of UVA and had a protective effect of 31% in the presence of UVA.

Crude sophorolipids in concentrations of 0.125 µg/ml, 0.25 µg/ml and 0.5 µg/ml caused a reduction in cellular viability of 18%, 14% and 15% and had a protective effect of 47%, 7% and 18% respectively.

In the absence of an anti-radical agent, the viability of the cells after UVA irradiation was no more than 21%.

Table 9 shows the evaluation of the anti-radical effect of crude sophorolipids towards free radicals generated by UVA.

| Protective effect | Reference exposed to UVA | Acetate of vitamin E 200 µg/ml | Crude sophorolipids 0.125 µg/ml | Crude sophorolipids 0.5 µg/ml |
|---|---|---|---|---|
| | 0% | 31% | 47% | 18% |

It appears that crude sophorolipids efficiently and remarkably protect cells against free radicals generated by UVA.

EXAMPLE 8

Cosmetic Applications Based on Sophorolipids

1. Formulation examples

Tables 10 and 11 show the different types of formulations which are possible. The quantities shown are the weight with respect to the total composition weight.

2. Mode of introducing sophorolipids into the emulsions

The acid or crude forms of the sophorolipids can be introduced both into the oily phase and into the aqueous phase.

If they are to be introduced into the oily phase, they must be dissolved in the oily phase at 70° C. just before emulsification in the aqueous phase.

The sophorolipids can be introduced cold into lotions, shampoos or gels, at the end of the manufacturing process.

The sophorolipids can be introduced cold into lotions or shampoos, at the end of the manufacturing process.

3. Formulation preparation examples

The following abbreviations were used in the formulations below:

MPOB: methyl parahydroxybenzoate (preservative)

PCL: pure cellin

Phenonip: phenoxyethanol, methylparaben, ethylparaben, propylparaben, butylparaben (preservatives)

PPG: propylene glycol

Ozokerite: (petroleum mineral wax: thickening agent)

CAO: castor oil 3.1 Make-up removal gel

| A | Sophorolipids | 3% (i.e., 0.9% of active material) |
|---|---|---|
| B | Hydroxypropyl guar | |
| | Hydroxypropyl trimonium chloride | 0.3% |
| | Hydroxyethyl cellulose | 1% |
| | Water | 84.5% |
| C | Sodium methyl cocoyl taurate | 0.4% |
| | Water | 10% |
| D | Phenonip | 0.5% |
| | Nonoxynol 10 | 0.2% |
| | Fragrance | 0.10% |

Operational procedure:

Mix phase C, with moderate heating.

Hydrate phase B and gradually add phase C.

Prepare phase D, mix it with phase BC and finally, add sophorolipids.

Mix to obtain a homogeneous gel.

3.2 Moisturizing cream containing sophorolipids, oil-in water type emulsion

| A | Crude or acid sophorolipids | 2% (i.e., 0.6% active material) |
|---|---|---|
| | Phenonip | 0.5% |
| | Fragrance | 0.2% |
| B | Glycerol stearate | 4% |
| | PEG 150, distearate | 0.5% |
| | Cetearyl alcohol | 2% |
| | Sunflower seed oil | 2% |
| | Cetearyl octanoate | 1% |
| | Triglycerides | 8% |
| | Dimethicone | 0.5% |
| C | Water | 55.70% |
| D | Glycerine | 3% |
| | Carbomer 840 | 0.3% |
| | Triethanolamine | 0.3% |
| | Water | 20% |

Operational procedure:

Prepare phase D: add, in order, glycerine, carbomer and water, then the triethanolamine.

Heat B and C separately (65° C.) and slowly add B to C, with stirring.

Add D then reduce temperature to 30°–35° C., then add the sophorolipids followed by preservative and fragrance.

3.3 Moisturizing cream containing sophorolihids, water/oil type emulsion (HLB 4 to 7)

Formula (calculated for 50% vegetable oil):

| Calcium salt of sophorolipid obtained from: | |
|---|---|
| Acid sophorolipids | 10% (4% dry matter) |
| Ca(OH)$_2$ | 10% |
| PPG** (stabilising agent) | 10% |
| Triglyceride sunflower oil and hydrogenated coconut oil** | 50% |
| Magnesium sulphate (methyl parahydroxybenzoate) | 4% |
| MPOB (parahydroxybenzoate) | 0.6% |
| Phenoxyethanol | 0.6% |
| Kathon | 0.2% |
| Fragrance | 0.2% |
| Water | 14.4% |

Operational procedure:

Heat water to 70° C.

Add sophorolipids and Ca(OH)$_2$, then the sulphate.

melt the oils (**) then incorporate them into the water.

add MPOB and phenoxyethanol preservatives at 40° C. and add Kathon and fragrance.

Tests were carried out with 20%, 40% and 50% of coconut oil.

3.4 Grease mixture, lipstick type (HLB 4–5)
Formula:

|  |  |
|---|---|
| Calcium salt of crude or acid sophorolipids | 4.0% |
| Strawberry flavour | 0.4% |
| Castor oil | 39.2% |
| Isopropyl merystate | 13% |
| Liquid PCL | 7.6% |
| White beeswax | 3.4% |
| Candelila wax | 7.2% |
| Carnauba wax | 2.3% |
| Ozokerite | 5.4% |
| Bintome CAO (gelling agent) | 6.9% |
| Amerlate W (lanoline derivative) | 7.6% |
| Ceraphyl 424 (fatty ester) | 3% |
| Propylparaben | 0.10% |

In this formulation, the emulsifying properties show the wetting character of the sophorolipid in its divalent alkaline salt form, with a low HLB.

We claim:

1. A method of inhibiting free radical formation or elastase activity in a patient in need thereof, which comprises administering to said patient an effective amount of a sophorolipid capable of inhibiting free radical formation or elastase activity, wherein the sophorolipid is in protonated acid form, in metallic salt form, or in crude form.

2. The method according to claim 1, wherein the composition is in the form of a water-in-oil emulsion, an oil-in-water emulsion or an oil-in-water microemulsion.

3. The method according to claim 2, wherein the compositions is an emulsion with a continuous oily phase wherein the oils phase is a vegetable oil.

4. A method of claim 3, wherein the vegetable oil is olive oil, sweet almond oil, walnut oil, or a hydrogenated coconut oil.

5. The method according to claim 1, wherein the composition contains as a sole emulsifying agent, said sophorolipid.

TABLE 10

COSMETIC APPLICATIONS USING SOPHOROLIPIDS

|  |  |  | Nature of sophorolipid | pH conditions | Quantity of sophorolipids | Water | Oil |
|---|---|---|---|---|---|---|---|
| EMULSIONS | Oil in water | Cream | Acid Crude Monovalent alkaline salt | 4 to 6 | 0.5 to 10% | 30 to 90% | 10 to 70% |
|  |  | Milk | Acid Crude Monovalent alkaline salt | 4 to 6 | 0.5 to 10% | 30 to 90% | 10 to 70% |
|  | water in oil | Cream | Divalent salts | — | 0.5 to 10% | 30 to 70% | 30 to 70% |
| FATTY MIXTURE |  |  | Divalent salts | — | 0.5 to 10% | 0% | 90 to 99.5% |
| AQUEOUS MICROEMULSIONS |  | Shower gel | Acid Crude Monovalent alkaline salt | 6 to 9 | 0.5 to 30% | 70 to 95% | 0 to 5% |
|  |  | Fragranced lotion | Acid Crude Monovalent alkaline salt | 6 to 9 | 0.5 to 30% | 70 to 95% | 0 to 5% |
|  |  | Shampoo | Acid Crude Monovalent alkaline salt | 6 to 9 | 0.5 to 30% | 70 to 95% | 0 to 5% |
|  |  | Liquid soap | Acid Crude Monovalent alkaline salt | 6 to 9 | 0.5 to 30% | 70 to 95% | 0 to 5% |

TABLE 11

|  | Nature of sophorolipid | pH conditions | Quantity of sophorolipids | Water | Alcohol | Oil |
|---|---|---|---|---|---|---|
| OLEO-ALCOHOLIC SOLUTION (fragranced lotion or milk) | Acid Crude Monovalent alkaline salt | 6 to 9 | 0.5 to 30% | 10 to 60% | 10 to 60% | 0 to 10% |
| HYDROALCOHOLIC PERFUME | Acid Crude Monovalent alkaline salt | 6 to 9 | 0.5 to 30% | 10 to 80% | 10 to 80% | — |

6. The method according to claim 1, wherein the composition comprises a sophorolipid and a conventional emulsifying agent.

7. The method according to claim 1, wherein the sophorolipid is dissolved in an oily phase, an aqueous solution, an alcoholic solution, an oleoalcoholic solution, or a hydroalcoholic solution.

8. The method according to claim 1, wherein the concentration of sophorolipids is in the range 0.01% to 30% by dry weight with respect to the total composition.

9. The method according to claim 1, wherein the composition comprises at least one fatty acid having 10 to 34 carbon atoms in a proportion of 0.01% to 20% by weight with respect to the sophorolipids.

10. The method according to claim 1, wherein the composition is administered topically.

11. The method of claim 1 wherein free radical formation is inhibited.

12. The method of claim 1 wherein elastase activity is inhibited.

13. The method of claim 1, wherein the sophorolipid is in a protonated acid form.

14. The method of claim 1, wherein the sophorolipid is in metallic salt form.

15. The method of claim 1, wherein the sophorolipid is in crude form.

16. The method of claim 1, wherein the formation of free radicals by UV-A is inhibited.

17. A method of protecting against UV-A damage in a patient in need thereof, comprising administering to said patient a composition comprising an effective UV-A protecting amount of a sophorolipid capable of inhibiting free radical formation, wherein the sophorolipid is in protonated acid form, in metallic salt form, or in crude form.

18. A method of protecting against UV-A damage in a patient in need thereof, comprising administering to said patient an effective amount of a composition comprising an effective UV-A protecting amount of a sophorolipid, wherein the sophorolipid is in protonated acid form, in metallic salt form, or in crude form.

* * * * *